(12) United States Patent
Song

(10) Patent No.: US 8,160,822 B2
(45) Date of Patent: Apr. 17, 2012

(54) APPARATUS AND METHOD FOR MEASURING OPTIMUM WATER QUALITY AND INFORMING QUALITY OF WATER

(75) Inventor: Seung June Song, Seoul (KR)

(73) Assignees: Sechang Instruments Co., Ltd., Seoul (KR); Seung June Song, Seoul (KR)

( * ) Notice: Subject to any disclaimer, the term of this patent is extended or adjusted under 35 U.S.C. 154(b) by 386 days.

(21) Appl. No.: 12/518,984

(22) PCT Filed: Dec. 17, 2007

(86) PCT No.: PCT/KR2007/006576
§ 371 (c)(1),
(2), (4) Date: Jun. 12, 2009

(87) PCT Pub. No.: WO2008/075861
PCT Pub. Date: Jun. 26, 2008

(65) Prior Publication Data
US 2010/0082265 A1    Apr. 1, 2010

(30) Foreign Application Priority Data
Dec. 19, 2006  (KR) .......................... 10-2006-0130057

(51) Int. Cl.
*G01N 33/18*  (2006.01)
*G06F 19/00*  (2011.01)

(52) U.S. Cl. ......... 702/25; 210/321.6; 436/125; 702/81; 702/156

(58) Field of Classification Search .............. 702/25, 702/30, 31, 32, 55, 81, 100, 156, 177, 182; 210/85, 321.6, 709; 436/125
See application file for complete search history.

(56) References Cited

U.S. PATENT DOCUMENTS

| 5,628,895 A * | 5/1997 | Zucholl ......................... 210/85 |
| 6,241,896 B1 * | 6/2001 | La Fargue, Jr. ............... 210/709 |
| 6,607,668 B2 * | 8/2003 | Rela ........................... 210/321.6 |
| 6,753,186 B2 | 6/2004 | Moskoff |

FOREIGN PATENT DOCUMENTS

| JP | 2003-103250 A | 4/2003 |
| KR | 10-2001-0035534 A | 5/2001 |
| KR | 10-2006-0098704 A | 9/2006 |

OTHER PUBLICATIONS

International Search Report for PCT/KR2007/006576, dated Mar. 26, 2008.

* cited by examiner

*Primary Examiner* — John H Le
(74) *Attorney, Agent, or Firm* — Bachman & LaPointe, P.C.

(57) ABSTRACT

An apparatus for measuring optimum water-quality and informing quality of water 100 measures an amount of impurities of water, keeps to renew an optimum value by a lowest amount of the impurities until the present use, compares the optimum value with the present amount of the impurities measured in the water and informs the result.

34 Claims, 12 Drawing Sheets

(a)   (b)

APPARATUS AND METHOD FOR MEASURING OPTIMUM WATER QUALITY AND INFORMING QUALITY OF WATER

FIELD OF THE INVENTION

The present invention relates to an apparatus and method for measuring and informing water quality, and more particularly to an apparatus and method which are adapted to measure optimum water-quality in connection with water service pipe and inform quality of the water.

BACKGROUND

Water service pipe is a path along which water is supplied and, for example, in water supply system, the pipe is connected from purification plant to home and water is supplied to the home along the pipe.

Generally, water which flows along the pipe contains impurities such as rust from the pipe, and the water discharged from the pipe when water-valve is just open contains the most amount of the impurities, and the amount of the impurities of the discharged water from the pipe reduces as the opening-hour of the water-valve becomes longer. This is because the impurities such as the rust on the pipes are washed out as the water flows out.

Accordingly, the amount of the impurities of the discharged water reduces as time goes on after the open of the water-valve and, generally, the amount of the impurities of the discharged water becomes the lowest when the water-valve is closed and the water-supply is terminated. That is, unless the event such as inflow of foreign substances happens, the discharged water contains the lowest impurities when the water-supply is terminated.

When the use of the water is resumed after the use of the water started by opening the water-valve is completed by closing the water-valve, the impurities such as the rust generated during the close of the water-valve are discharged along with the water at the initial time and, if the use of the water is kept after the all-exhaustion of the impurities generated during the close of the water-valve, the amount of the impurities of the water reduces furthermore and becomes smaller than the lowest amount of the impurities in the former use over some time.

Accordingly, along the time of the use of the water until present time, a point of the lowest amount of the impurities that the discharged water contains exists and this becomes optimum amount of the impurities until the present use in connection with the water service pipe. That is, the water at the point contains the lowest impurities among the discharged water from the water service pipe until now.

There is a desire to use water having optimum quality (that is, the amount of the impurities in the water is the lowest until the present use), for example, a user wants to drink the water having the optimum quality. The present invention satisfies this demand.

DISCLOSURE

Technical Problem

The purpose of the present invention is to provide an apparatus and method for measuring optimum water-quality and informing quality of water, which can check whether the water discharged from water service pipe contains the lowest amount of impurities among the discharged water until now and inform the present quality of the discharged water.

Technical Solution

The present invention provides an apparatus for measuring optimum water-quality and informing quality of water comprising: an impurities-detecting part for detecting an amount of impurities of water; a control part coupled with the impurities-detecting part, wherein the control part stores an initial optimum value, the optimum value indicating the optimum amount of the impurities of the water, the control part including, measurement means for measuring the amount of the impurities of the water which receives a signal for the amount of the impurities of the water from the impurities-detecting part and measures it, renewal time decision means for deciding whether it is a renewal time of the optimum value, comparison means for comparing the amount of the impurities of the water measured by the measurement means with the optimum value. and optimum-value renewal means for renewing the optimum value by the amount of the impurities of the water if the comparison result made by the comparison means is that the amount of the impurities of the water is smaller than the optimum value, if it is decided as the renewal time by the renewal time decision means; informing part for informing the result of the comparison by the comparison means.

According to the present invention, the control part stores a renewal period and the renewal time decision means includes renewal time decision means by renewal period which decides the renewal time by every renewal period.

According to the present invention, the apparatus for measuring optimum water-quality and informing quality of water further includes an input part for setting the renewal period coupled with the control part.

According to the present invention, the apparatus for measuring optimum water-quality and informing quality of water further includes an input part for requesting the renewal coupled with the control part and the renewal time decision means includes renewal time decision means by input of the renewal request which decides as the renewal time if the renewal request is inputted by the input part for requesting the renewal.

According to the present invention, the apparatus for measuring optimum water-quality and informing quality of water further includes a water-supply termination detecting sensor for detecting whether the water-supply is terminated coupled with the control part and the renewal time decision means includes renewal time decision means by the termination of the water-supply which decides as the renewal time if it is decided that the water-supply is terminated according to the water-supply termination detecting sensor.

According to the present invention, the impurities-detecting part detects an electric conductivity of the water.

According to the present invention, the impurities-detecting part detects a turbidity of the water.

According to the present invention, the impurities-detecting part detects residual chlorine of the water.

According to the present invention, the impurities-detecting part detects an ion concentration for particular ion of the water.

According to the present invention, the impurities-detecting part detects a hydrogen ion concentration (PH) of the water.

According to the present invention, if attribute of the impurities detected by the impurities-detecting part has allowable range according to water quality standard, the optimum value is determined by an absolute value of deviation of the allowable value from an inherent optimum value and the amount of the impurities of the water is determined by an absolute value of deviation of the amount of the impurities of the water from the inherent optimum value.

According to the present invention, the impurities-detecting part detects a hydrogen ion concentration (PH) of the water.

According to the present invention, the water-supply termination detecting sensor is a current meter and the renewal time decision means by the termination of the water-supply decides as the renewal time if fluid velocity detected by the current meter is below a particular value.

According to the present invention, the impurities-detecting part detects an electric conductivity of the water and this impurities-detecting part is used as the water-supply termination sensor, and the renewal time decision means by the termination of the water-supply decides as the renewal time if the conductivity of the water detected by the impurities-detecting part is below a particular value.

According to the present invention, the impurities-detecting part detects a turbidity of the water and this impurities-detecting part is used as the water-supply termination sensor, and the renewal time decision means by the termination of the water-supply decides as the renewal time if the turbidity of the water detected by the impurities-detecting part is below a particular value.

According to the present invention, the apparatus for measuring optimum water-quality and informing quality of water further includes a pipe part having a stay part at which the flowing water stays is formed and a detecting terminal of the impurities-detecting part is placed at the stay part.

According to the present invention, the water-supply termination detecting sensor includes, an electrode and a circuit part for sensing conductivity of the water flowing around the electrode and the renewal time decision means by the termination of the water-supply decides as the renewal time if the conductivity of the water is below a particular value.

According to the present invention, the informing part informs that the water quality is good if the amount of the impurities of the water is smaller than the optimum value.

According to the present invention, the informing part informs whether the water is suitable according to water quality standard.

According to the present invention, the informing part informs that the water-quality is good if deviation of the amount of the impurities of the water from the optimum value is within some range.

According to the present invention, the apparatus for measuring optimum water-quality and informing quality of water further includes a reset part for initializing the optimum value.

According to the present invention, the apparatus for measuring optimum water-quality and informing quality of water is installed in a water purifier or a water feeder for drinking.

According to the present invention, the apparatus for measuring optimum water-quality and informing quality of water further includes a water-supply detecting sensor for detecting whether the water is supplied.

According to the present invention, the water-supply detecting sensor is a water-flow detecting sensor.

According to the present invention, the water-flow detecting sensor includes a buoyancy mechanism and a relay connected therewith.

According to the present invention, the apparatus for measuring optimum water-quality and informing quality of water further includes a self power-generation which generates power by the flow of the water supplied thereto and is operated by the self generated power.

Also, the present invention provides an apparatus for measuring optimum water-quality and control comprising: an impurities-detecting part for detecting an amount of impurities of water; a control part coupled with the impurities-detecting part, wherein the control part stores an initial optimum value, the optimum value indicating the optimum amount of the impurities of the water, the control part including, measurement means for measuring the amount of the impurities of the water which receives a signal for the amount of the impurities of the water from the impurities-detecting part and measures it, renewal time decision means for deciding whether it is a renewal time of the optimum value, comparison means for comparing the amount of the impurities of the water measured by the measurement means with the optimum value. and optimum-value renewal means for renewing the optimum value by the amount of the impurities if the amount of the impurities of the water measured by the measurement means is smaller than the optimum value, if it is decided as the renewal time by the renewal time decision means; control-signal output part for outputting a control signal for controlling an actuator according to the result of the comparison by the comparison means.

Further, the present invention provides a method for measuring optimum water-quality and informing quality of water comprising: initial optimum value storage step where a control part stores an initial optimum value, the optimum value indicating the optimum amount of the impurities of the water; impurities measurement step where the control part measures an amount of impurities of water by a signal from an impurities-detecting sensor for detecting an amount of impurities of the water; renewal time decision step where the control part decides whether it is a renewal time of the optimum value; comparison step where the control part compares the amount of the impurities of the water with the optimum value; optimum-value renewal step where the control part renews the optimum value by the amount of the impurities if the amount of the impurities of the water measured by the measurement means is smaller than the optimum value, if it is decided as the renewal time by the renewal time decision step; optimum water-quality inform step where the control part informs the result of the comparison by the comparison step through an informing part.

According to the present invention, the renewal time decision step includes renewal time decision step by termination of water-supply where the control part decides as the renewal time if it is decided that the water-supply is terminated according to a water-supply termination detecting sensor for detecting whether the water-supply is terminated.

According to the present invention, the renewal time decision step includes renewal time decision step by renewal period where the control part stores a renewal time and it decides the renewal time by every renewal period.

According to the present invention, renewal time decision step includes renewal time decision step by input of renewal request where the control part decides as the renewal time if the renewal request is inputted.

The present invention provides a computer readable storage medium recording the steps.

Furthermore, the present invention provides a management computer connected with an apparatus for measuring optimum water-quality and informing quality of water via communication network, the management computer managing data received from the apparatus, the apparatus comprising: an impurities-detecting part for detecting an amount of impurities of water; a control part coupled with the impurities-detecting part, wherein the control part stores an initial optimum value, the optimum value indicating the optimum amount of the impurities of the water, the control part including, measurement means for measuring the amount of the impurities of the water which receives a signal for the amount of the impurities of the water from the impurities-detecting part and measures it, renewal time decision means for deciding whether it is a renewal time of the optimum value, comparison means for comparing the amount of the impurities of the water measured by the measurement means with the optimum value. and optimum-value renewal means for renewing the optimum value by the amount of the impurities if the amount of the impurities of the water measured by the measurement means is smaller than the optimum value, if it is decided as the renewal time by the renewal time decision means; impurities storage means by every time for storing the amount of the impurities of water by every time; impurities-data sending means for sending the amount of the impurities of the water stored by the impurities storage means to the management computer.

According to the present invention, the control part of the apparatus further includes optimum value storage means for storing the optimum value by every time and optimum-value data sending means for sending the optimum value stored by the impurities storage means to the management computer.

Advantageous Effects

The present invention provides the apparatus and method which checks whether the water discharged from the particular water service pipe contains the lowest impurities among the discharged water until present time and informs the present quality of the discharged water.

The present invention searches the lowest impurities of the water which the water service pipe can accomplish from the past use to the present use and informs that the water is optimum if the impurities of the water are below the lowest impurities.

The present invention makes it possible to deal with a water pollution accident.

MODE FOR INVENTION

Now, the preferred embodiment of the present invention will be explained with reference to the accompanying drawings.

Figure 1:
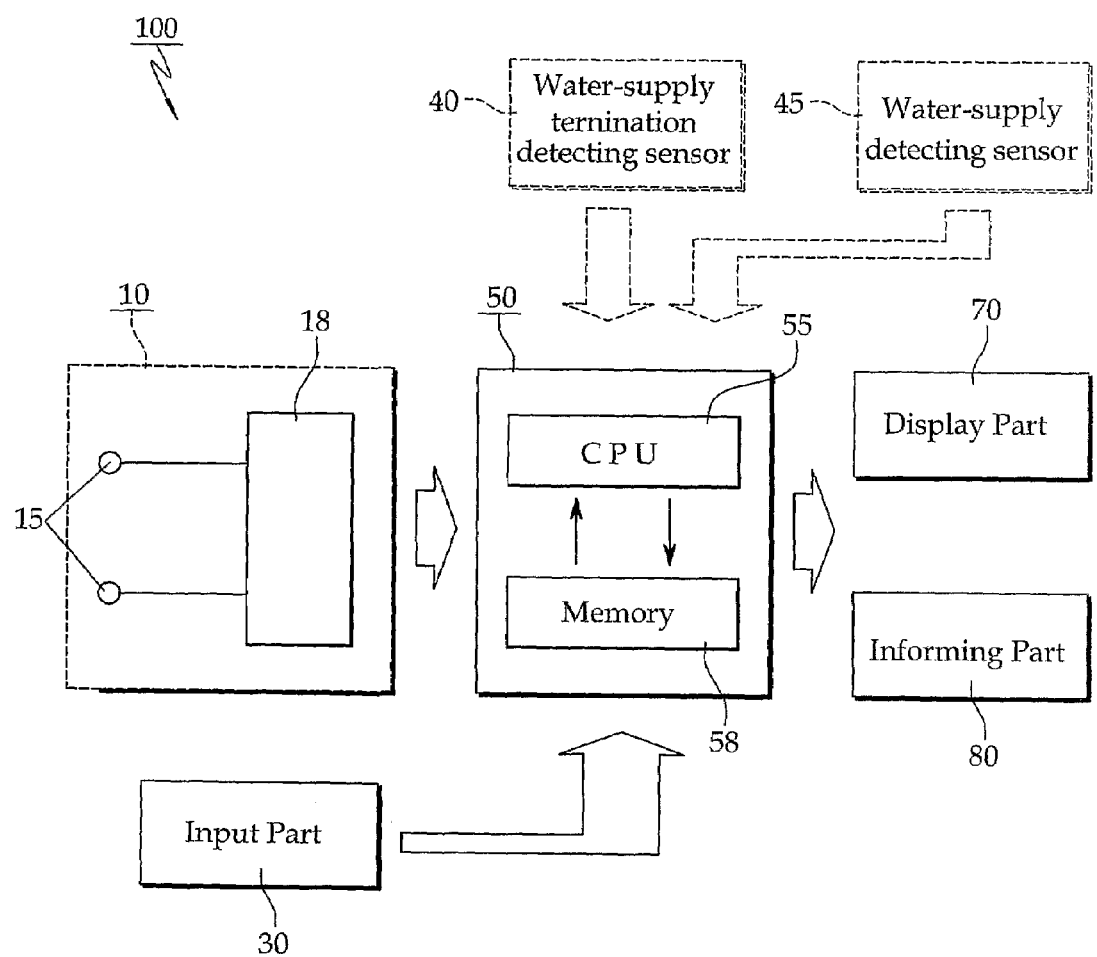
FIG. 1 is a view showing configuration of an apparatus for measuring optimum water-quality and informing quality of water in accordance with an embodiment of the present invention.

FIG. 1 is a view showing configuration of an apparatus for measuring optimum water-quality and informing quality of water 100 in accordance with an embodiment of the present invention.

The apparatus 100 has an impurities-detecting part 10 for detecting an amount of impurities of water.

The impurities-detecting part 10 has a detecting terminal 15 and a circuit part 18 which electrically processes the signal from the detecting terminal 15. The circuit part 18 electrically processes the signal which the detecting terminal 15 detects and the processed signal is sent to a control part 50 and the control part 50 measures the amount of the impurities of the water. For measuring an amount of the impurities of the water, various kind of attributes of water can be detected according to the water quality standard. For example, electric conductivity of the water, turbidity of the water, residual chlorine or ion concentration indicating hydrogen ion concentration (PH) or specific pollutants such as Pb, fluorine, ammonia nitrogen and nitrite nitrogen can be detected by the impurities-detecting part 10.

If the impurities-detecting part 10 detects the electric conductivity of the water, like a conventional TDS (Total Dissolved Solid) tester, electrodes are provided as the detecting terminal 15 and the circuit part 18 senses the electric conductivity of the water flowing around the electrodes and, accordingly, the control part 50 measures an amount of the impurities of the water according to the electric conductivity.

If the impurities-detecting part 10 detects the turbidity of the water, like a conventional turbidity meter, a light source emitting light to the water and a light receiver receiving the light emitted from the light source are provided as the detecting terminal 15 and a light converting transducer which converts strength of the light received by the light receiver to voltage and outputs it is provided as the circuit part 18. The control part 50 measures the turbidity according to the voltage inputted from the light converting transducer 18.

Generally, there are various methods for measuring the turbidity such as transmitted light method, scattered light method, surface scattering light method, and a transmitted-scattered light method. The present invention can employ such a various methods.

If the impurities-detecting part 10 detects a residual chlorine of the water, like a conventional residual chlorine meter, electrodes according to galvani electrode method or polarography method so on is provided as the detecting terminal 15 and diffusion current or the strength of electromotive force flowing the electrode is inputted to the control part 50 through the circuit part 18 and, accordingly, the control part 50 measures the residual chlorine of the water.

If the impurities-detecting part 10 detects a hydrogen ion concentration (PH), like a conventional hydrogen ion concentration meter, electrode for detecting the hydrogen ion is provided as the detecting terminal 15 and the circuit part 18 inputs the detected voltage or current from the electrode to the control part 50 and, accordingly, the control part 50 measures the hydrogen ion concentration of the water.

If the impurities-detecting part 10 detects the ion concentration, like an conventional ion concentration meter or ion sensor, an ion electrode and a comparison electrode are provided as the detecting terminal 15 and the detected potential difference or current by the circuit part 18 is inputted to the control part and, accordingly, the control part 50 measures the ion concentration of the water.

The control part 50 includes a CPU 55 and a memory 58. The CPU 55 includes a microprocessor and the memory 58 includes ROM or RAM and stores a program deciding the operation of the CPU 55 and data which the CPU 55 processes.

Also, the apparatus for measuring optimum water-quality of water and informing quality of water 100 may have an input part 30. In this case, an optimum amount of the impurities of the water which a user want can be inputted to and set in the control part 50. In other case, as described later, renewal period for an optimum amount of the impurities of the water can be inputted and set. Further, it is possible to input a request for renewal of the optimum amount of the impurities of the water.

The input part 30 can be various forms such as a button or a key board. The values such as the optimum amount of the impurities of the water or the renewal period for the optimum amount of the impurities of the water can be initially set in the memory 58 by maker independent of the input part 30.

The optimum amount of the impurities of the water becomes an optimum value and the optimum value which is initially set and stored becomes an initial optimum value. This will be described later.

According to the present invention, it is necessary to decide whether it is a renewal time of the optimum value, which is the optimum amount of the impurities of the water, and to decide whether to renew the optimum value if it is decided as the renewal time of the optimum value.

For this, water-supply termination detecting sensor 40 which detects whether water-supply is terminated can be provided. In this case, the control part 50 decides whether the water-supply is terminated through the water-supply termination detecting sensor 40 and decides as the renewal time of the optimum value if it is decided that the water-supply is terminated. The present invention can employ various types of the water-supply termination detecting sensor 40 as described later.

The control part 50 continuously renews the optimum amount of the impurities of the water (the optimum value), compares it with the amount of the impurities of the water measured through the impurities-detecting part 10, informs the result through an informing part 80 and, additionally, displays necessary things through a display part 70.

According to the present invention, water-supply detecting sensor 45 which detects whether water is supplied can be provided. For example, a fluid-flow detecting sensor can be provided.

If the water is supplied through the water service pipe, the water-supply detecting sensor 45 such as the fluid-flow detecting sensor detects the flow of the water and, then, the apparatus for measuring optimum water-quality and informing quality of water 100 operates. For example, a power-relay switch which is relayed by the flow of the fluid can be provided.

Specifically, the power-relay switch which is relayed by the flow of the fluid can be a power-relay switch connected with a buoyancy mechanism. The buoyancy mechanism relays the power-relay switch when the water is supplied so that power is applied and the apparatus for measuring optimum water-quality and informing quality of water 100 operates.

In other case, a power-relay switch connected with a leverage mechanism can be provided as the power-relay switch which is relayed by the flow of the fluid. The water flow moves the leverage mechanism to relay the power-relay switch and the power is applied.

Figure 2:
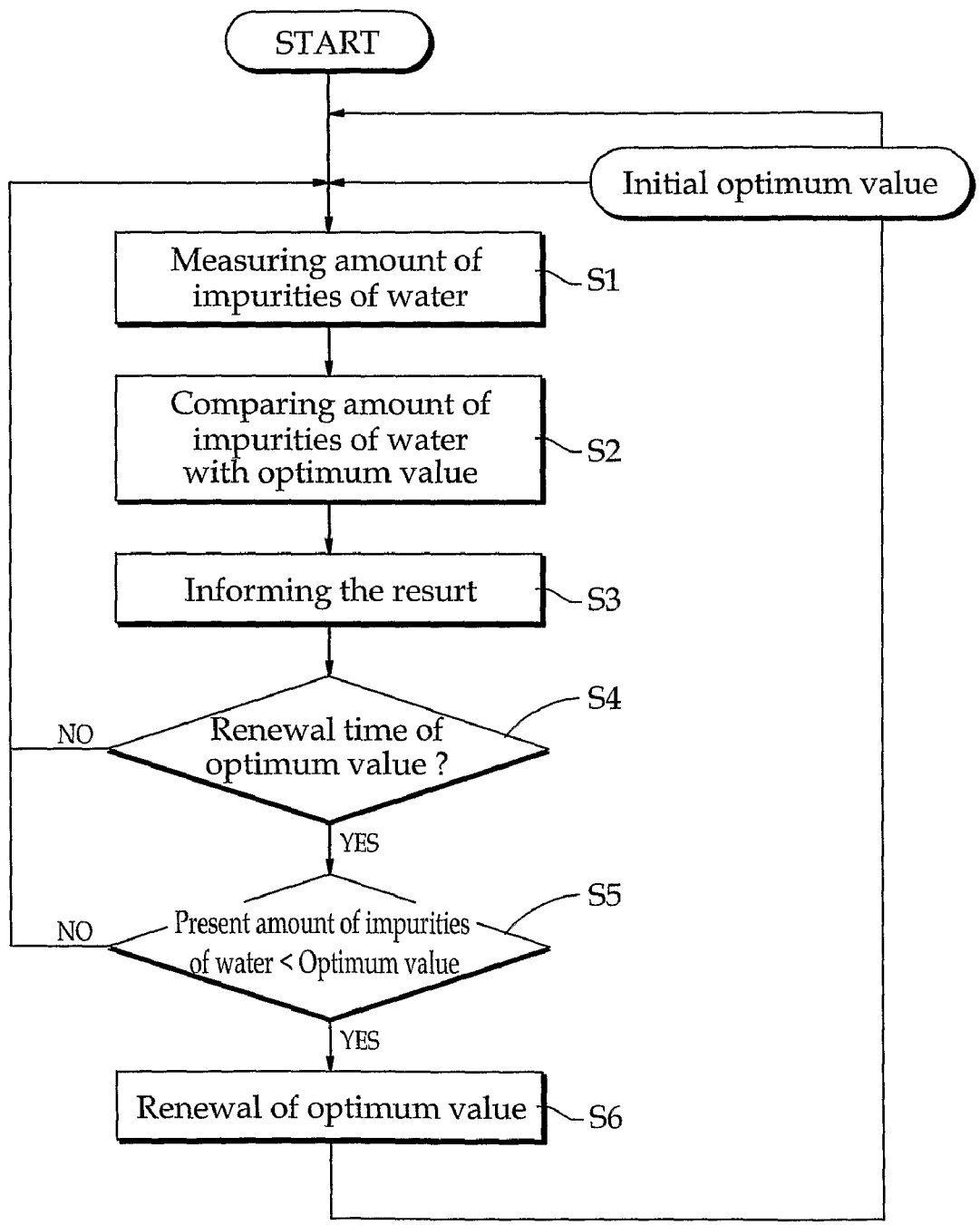
FIG. 2 is a flow chart showing the operation of the control part of the apparatus for measuring optimum water-quality and informing quality of water.

FIG. 2 is a flow chart showing the operation of the control part 50 of the apparatus for measuring optimum water-quality and informing quality of water 100.

Firstly, the control part 50 measures the present amount of the impurities of the water according to the signal from the impurities-detecting part 10. (STEP S1)

Then, the control part 50 compares the measured amount of impurities with the optimum value. (STEP S2) If it is initial use, the control part 50 compares the measured amount of impurities with the initial optimum value stored on the memory 58.

Then, the control part 50 informs the result of the comparison through the informing part 80. (STEP S3) In this case, if the present amount of the impurities of the water is smaller than the optimum value, it is informed that the water is good and useful for, for example, drinking so on.

Then, the control part 50 decides whether it is the renewal time of the optimum value. (STEP S4) If it is decided as the renewal time of the optimum value, the control part 50 compares the measured amount of the impurities of the water at present with the optimum value. (STEP S5)

If the present amount of the impurities of the water is smaller than the optimum value, the control part 50 renews the optimum value by the present amount of the impurities and stores it in the memory 58. (STEP S6)

Accordingly, if the use is the first time, the optimum value is renewed if the present amount of the impurities of the water is smaller than the initial optimum value at the renewal time and, otherwise, the optimum value is kept by the stored initial optimum value.

After the first use, the optimum value is renewed by the present amount of the impurities of the water if the present amount of the impurities of the water is smaller than the optimum value renewed before at the renewal time.

By this way, according to the present invention, the lowest amount of the impurities of the water until the present time is renewed as the optimum value and whether the present amount of the impurities is smaller than the optimum value is informed through the informing part 80. Accordingly, a user can recognize whether the water from the water service pipe is in the optimum status.

According to the present invention, the decision whether it is the renewal time in the step S4 is accomplished by various ways.

For example, the memory 58 of the control part 50 remembers a renewal period and the control part 50 decides that it is the renewal time if the renewal period arrives. The renewal period is initially set and stored in the memory 58 or, in other case, a user can input the renewal period and set it through the input part 30. The renewal period can be stored by, for example, every 1 hour, every 30 minutes or every 10 minutes.

In other case, the apparatus for measuring optimum water-quality and informing quality of water 100 may have a button for requesting the renewal as the input part 30 and the control part 50 can decide it as the renewal time if the button is pressed.

Also, according to the present invention, the water-supply termination detecting sensor 40 is provided and the control part 50 decides whether the water-supply is terminated through the sensor 40 and decides that it is the renewal time if it is decided that the water-supply is terminated.

Especially, if the water-supply termination detecting sensor 40 is provided and the control part 50 decides that it is the renewal time since the water-supply is terminated, the optimum value is renewed by the lowest amount of the impurities until the present use.

According to the present invention, the control part 50 can determine the amount of the impurities of the water by direct value measured by the signal from the impurities-detecting part 10. Also, the control part 50 can determine the amount of the impurities of the water by the average value measured by the signal from the impurities-detecting part 10 between time interval. For example, the average value of the particular time interval can be determined as the present amount of the impurities of the water.

Specifically, if the average value for 3 seconds is determined as the present amount of the impurities of water and the measured values every 1 second for 3 seconds are 49, 50 and 51, the average value 50 is determined as the present amount of the impurities of water and is compared with the optimum value.

According to the present invention, in connection with the steps S2 and S3, it is possible to compare the present amount of the impurities of the water with the water quality standard and inform it. In this case, the control part 50 may store the water quality standard readily set or inputted through the input part 30. For example, if the impurities-detecting part 10 detects the turbidity of the water, the turbidity should be below 0.5 NTU according to the water quality standard. The control part 50 remembers this standard and compares the measured turbidity of the water with the standard as well as the optimum value in the step S2. Accordingly, the control part 50 informs that the water-quality is suitable according to the water standard through the informing part 80 if the turbidity is below the standard (O.5 NTU) in connection with step S3. (Refer to FIG. 4)

The attribute such as electric conductivity, turbidity, residual chlorine and ion concentration indicating specific pollutants such as Pb, fluorine, ammonia nitrogen and nitrite nitrogen is better as the amount is smaller and, for example, the water quality standard fit for drinking defines the maximum allowable contents for them. However, in some cases, it is good if the attribute is within some range such as hydrogen ion concentration (As for the hydrogen ion concentration, the allowable range is within PH 5.8 to 8.5 according to the water quality standard fit for drinking). In this case, it may need absolute value of deviation of allowable value from inherent optimum value as the optimum value. Also it may need absolute value of deviation of the present amount of the impurities of the water from the inherent optimum value as the present amount of the impurities of the water in connection with steps S2 and S5.

For example, in case of hydrogen ion concentration (PH), PH 7 which is neutral may be the inherent optimum value and the optimum value will be the absolute value of the deviation of the allowable PH value from the inherent optimum value PH 7.

At the first use, a deviation from the inherent optimum value set in the memory 58 will become the initial optimum value and, hereafter, the renewed deviation at renewal time will become the optimum value Also, the absolute value of the deviation of the PH value of the water measured at present time from the inherent optimum value PH 7 will become the present amount of the impurities of the water. Accordingly, for example, if it is allowable to PH 7.5 or to PH 6.5 in connection with the inherent optimum value PH 7 at initial use, the initial optimum value will be 0.5.

Then, if the PH of the water measured at present time is 7.3 in connection with the step S2, the absolute value of the deviation from the inherent optimum value PH 7 is 0.3, which is smaller than the optimum value 0.5, so that the informing part 80 informs that it is good in connection with the step S3.

Further, if the PH of the water measured at the renewal time is 7.2 in connection with the step S5, the deviation is 0.2, which is smaller than the optimum deviation value 0.5, so that the optimum value is renewed in connection with the step S6.

According to the present invention, the impurities-detecting part 10 may be used as the water-supply termination detecting sensor 40.

If the impurities-detecting part 10 detects the electric conductivity of the water, it is possible to decide that the water-supply is terminated if the conductivity measured from the detecting electrode 15 falls down below a particular value. If the water-supply is substantially terminated, the water-flow is terminated and the conductivity of the electrode 15 will be zero or near zero so that it is possible to decide that the water-supply is terminated if the conductivity is zero or near zero.

If the impurities-detecting part 10 detects the turbidity of the water, it is possible to decide that the water-supply is terminated if the turbidity is zero or near zero.

In other case, the water-supply termination detecting sensor 40 may be current meter. The current meter 40 can be various forms. For example. electro magnetic type which checks fluid-velocity by the electromotive force generated by the moving fluid in the magnetic field, pressure type (differential pressure type) which checks fluid-velocity by the pressure generated by the fluid-flow or revolution type in which turbine, disc or impeller is provided and fluid-velocity is checked by the revolution of the turbine, disc or impeller by the movement of the fluid can be employed. In another case, type in which a pole is provided in the center of a pipe and fluid-velocity is checked by the vortex flow generated by the fluid passing the pipe. Further, the current meter 40 may be ultrasonic type which emits ultrasonic wave and checks fluid-velocity by the change of the reception of the ultrasonic wave.

Furthermore, the water-supply termination detecting sensor 40 includes a buoyancy mechanism and a relay connected therewith. When the water-supply is terminated, the buoyancy mechanism disconnects the relay and it is decided that the water-supply is terminated.

According to the present invention, in informing the result of the comparison of the present amount of the impurities of the water with the optimum value through the informing part 80 in connection with the steps S2 and S3, it is possible to inform that the water-quality is good and useful, for example, for drinking so on if the deviation of the present amount of the impurities of the water from the optimum value is within some range. This is to stably inform the good status of the water when the present amount of the impurities of the water continuously fluctuates. This deviation includes positive value and negative value.

Figure 3:
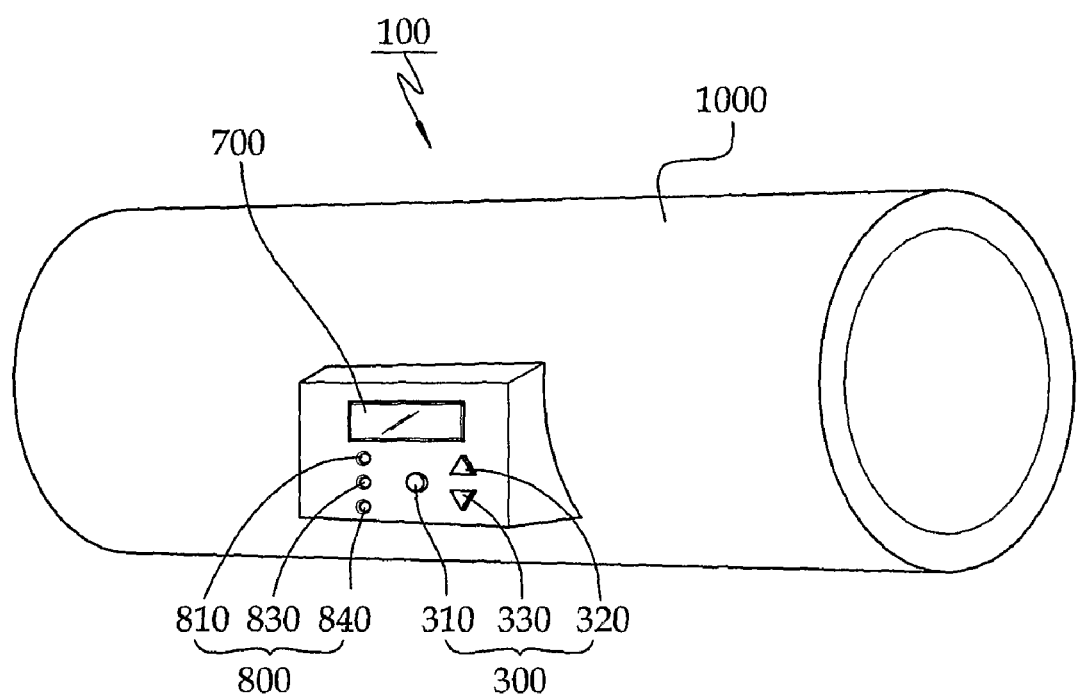
FIGS. 3 and 4 are views showing embodied products according to the apparatus for measuring optimum water-quality and informing quality of water.

FIG. 3 is a view showing an embodied product according to the apparatus for measuring optimum water-quality and informing quality of water 100.

In this case, a case 1000 is provided which is connected with the water service pipe and a display part 700, an informing part 800 and an input part for setting 300 are installed on a side of the case 1000.

The display part 700 is, for example, a LED display window and displays the present amount of the impurities of the supplied water detected from the impurities-detecting part 10.

The informing part 800 includes display lamps 810 and 830 and if the amount of the impurities of the supplied water is smaller than the optimum value, the blue lamp 810 is turned on and, otherwise, the red lamp 830 is turned on.

The informing part 800 further includes a display lamp 840 and if the supplied water satisfies the water quality standard, the green lamp 840 is turned on.

The input part for setting 300 by which a user can input and set the initial optimum value includes a setting button 310 and two arrow buttons 320 and 330 indicating upward and downward, respectively. A user presses the setting button 310 and, then, presses the arrow button 320 or 330 to define the optimum value which he wants to set up according to the displayed value on the display 700.

Figure 4:
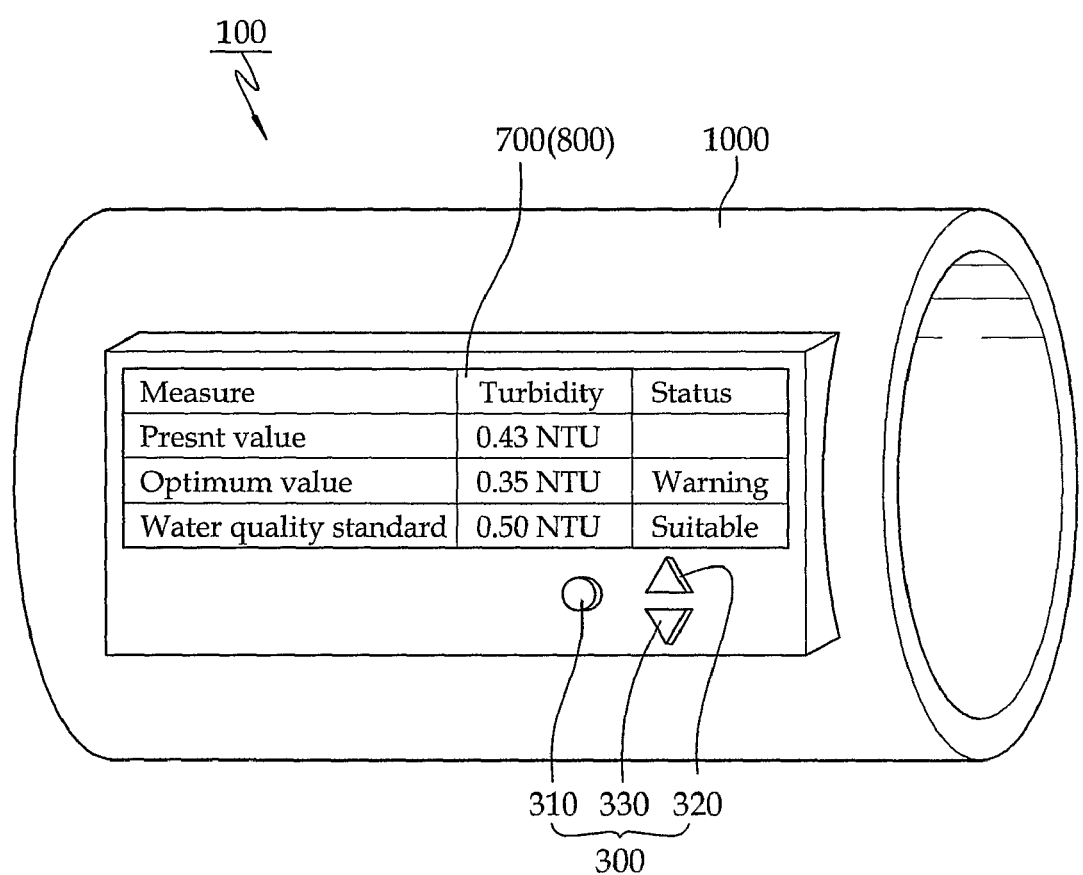

FIG. 4 is a view showing another embodied product according to the apparatus for measuring optimum water-quality and informing quality of water 100.

In this case, the display part 700 is provided by a LCD screen and also works as the informing part 800. That is, on the LCD screen, the present amount of the impurities of the water, whether the water is good because the amount of the impurities is smaller than the optimum value and whether the water is suitable in connection with the water quality standard are displayed and informed. Accordingly, the LCD screen works as the informing part 800 as well as the display part 700.

The LCD screen in FIG. 4 displays the present amount of the impurities of the water by the turbidity. It also displays that the measured turbidity of the water at present is 0.43 NTU and it is warning status because the measured turbidity is not smaller than the optimum value of 0.35 NTU, however, the water is suitable for drinking because the measured turbidity is smaller than the water quality standard 0.50 NTU.

Figure 5:
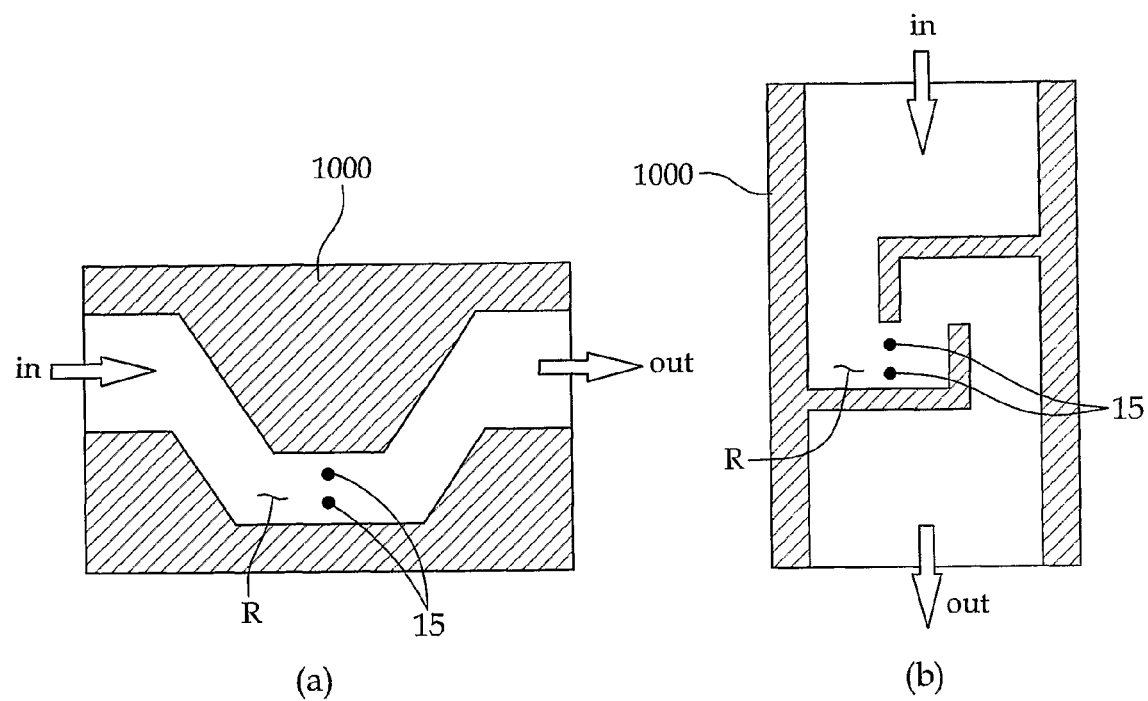
FIG. 5 is a view showing a cross section of a case in the apparatus for measuring optimum water-quality and informing quality of water.

According to the present invention, the cross section of the case 1000 having the shape of pipe may have a stay part R for the supplied water as shown in (a) and (b) of FIG. 5 and the electrodes or the light source and the light receiver are placed in the stay part R in order to detect the conductivity or the turbidity stably in spite of the fast water flow.

FIG. 5(*a*) shows that the stay part R is formed in a horizontal pipe. FIG. 5(*b*) shows that the stay part R is formed in a vertical pipe.

If the stay part R is formed in the apparatus for measuring optimum water-quality and informing quality of water 100 according to the present invention, the water can stay in the stay part R even if the water-supply is terminated so that it is impossible to decide that the water-supply is terminated if the measured conductivity or the turbidity is zero.

In this case, the current meter 40 can be provided in the stay part R and the control part 50 decides that the water-supply is terminated if the measured fluid-velocity is zero. The provision of the current meter is also applicable even if the stay part R is not provided.

According to the present invention, if the stay part R is provided, an electric conductivity-detecting part (not shown) including electrodes and circuit part coupled with the electrodes may be provided in other place than the stay part R in the case 1000 in order to decide whether the water-supply is terminated. If the conductivity measured by the electric conductivity detecting part is zero or near zero, it is possible to decide that the water-supply is terminated.

The stay part R is formed by the stay of the water in the case 1000 due to a head according to height of an external pipe connected therewith.

According to the present invention, a reset part may be provided for initializing the optimum value so that the previously stored optimum value can be initialized. For example, if the apparatus for measuring optimum water-quality and informing quality of water 100 was used for one water service pipe and then is used for another water service pipe, the optimum value stored for the previous use can be reset and initialized. It is also useful if a user wants to change the initial optimum value set by maker. Further, if a user wants to change the initial optimum value to correspond to the water quality standard, it is also useful.

Figure 6:
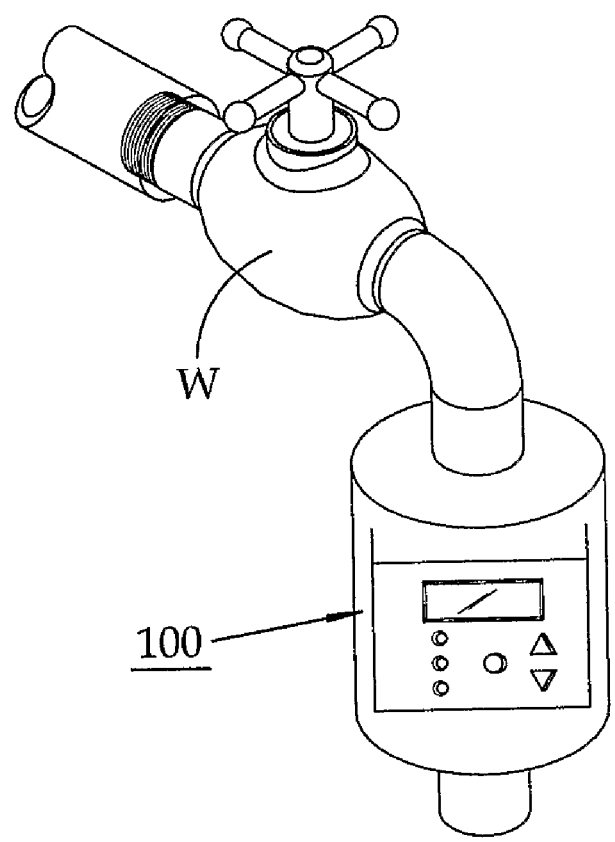
FIG. 6 is a view showing that the apparatus for measuring optimum water-quality and informing quality of water is connected with the water pipe.
Figure 6:
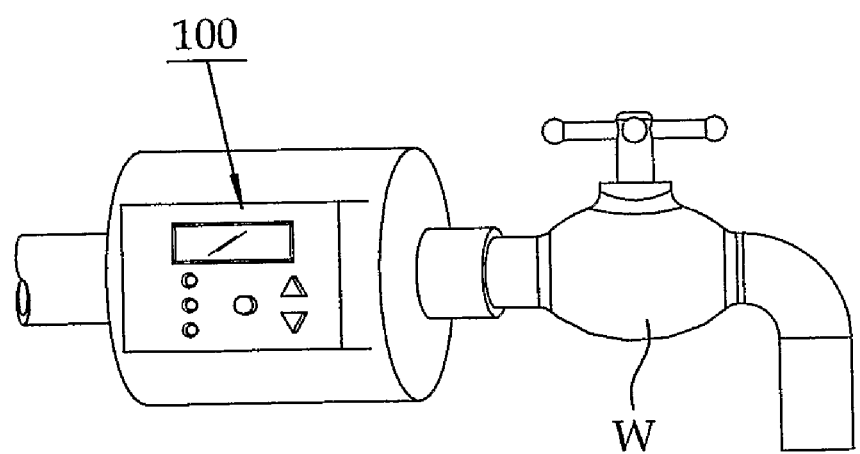

FIG. 6 is a view showing that the apparatus for measuring optimum water-quality and informing quality of water 100 is connected with the water pipe W. The upper view shows that the apparatus 100 is installed on the vertical part of the water valve and the bottom view shows that the apparatus 100 is installed on the horizontal part of the water valve.

Figure 7:
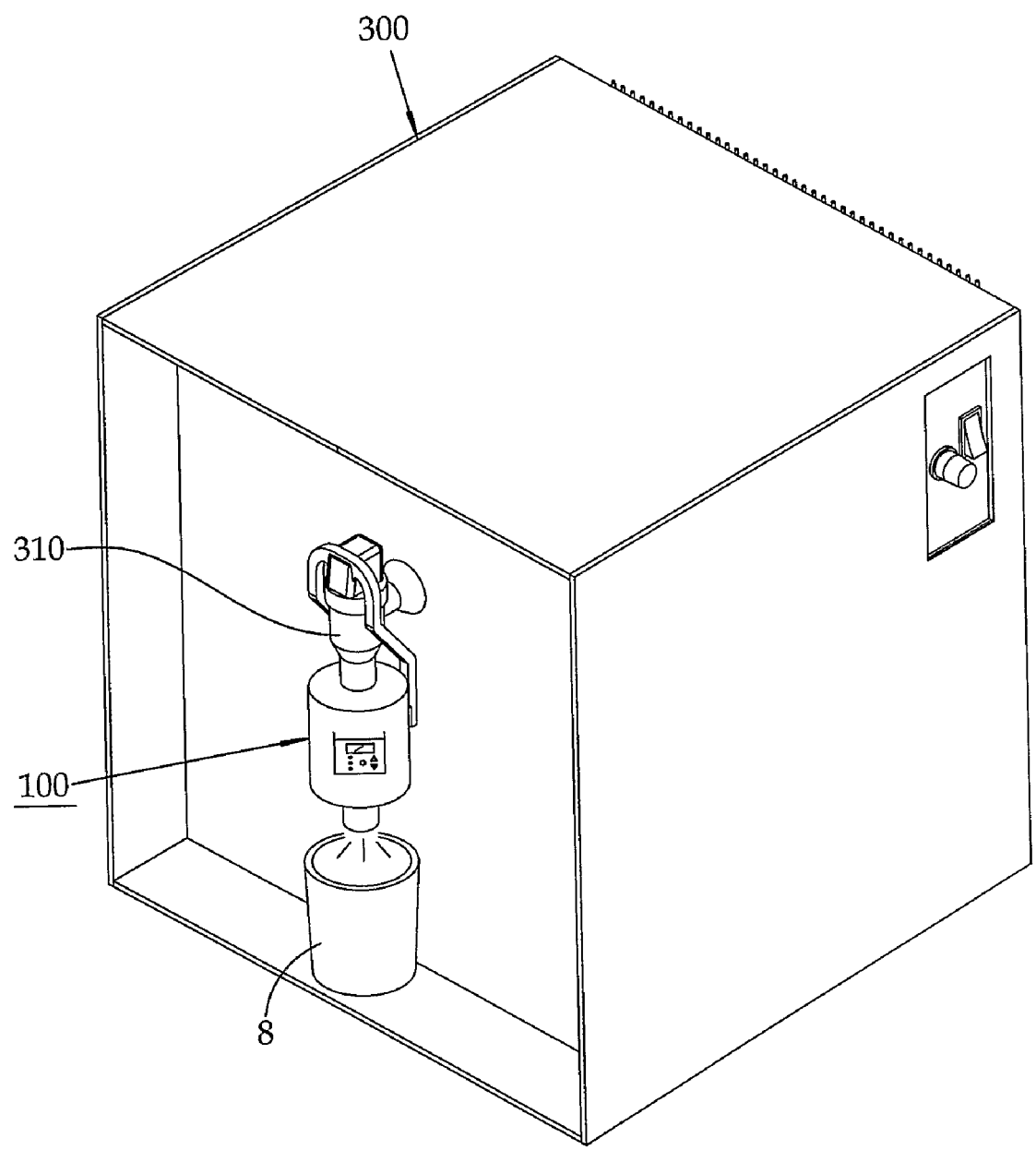
FIGS. 7 and 8 are views showing that the apparatus for measuring optimum water-quality and informing quality of the water is used for a water purifier.

FIG. 7 is a view showing that the apparatus for measuring optimum water-quality and informing quality of the water 100 is used for a water purifier 300. In this case, the water purifier 300 is connected with the water service pipe, purifies the water from the water service pipe and discharges the purified water. The apparatus for measuring optimum water quality and informing quality of water 100 is installed on a faucet 310 of the water purifier 300 and displays the optimum water quality of the water purifier 300. The numeral 8 indicates a cup.

Figure 8:
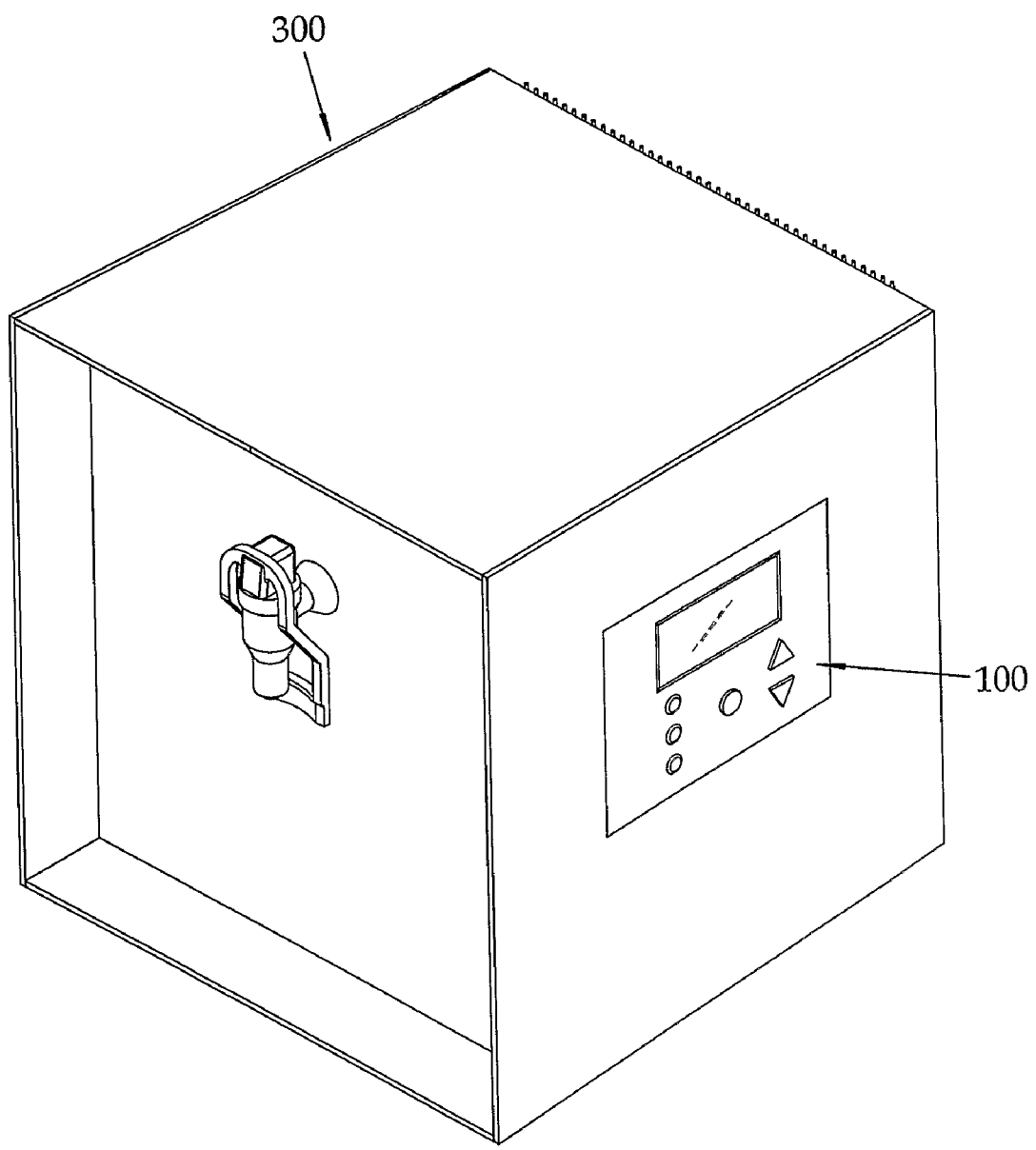

FIG. 8 is a view showing that the apparatus for measuring optimum water-quality and informing quality of water 100 is installed in the inner part of the water purifier 300 and displays the quality of the water supplied to the water purifier 300.

Figure 9:
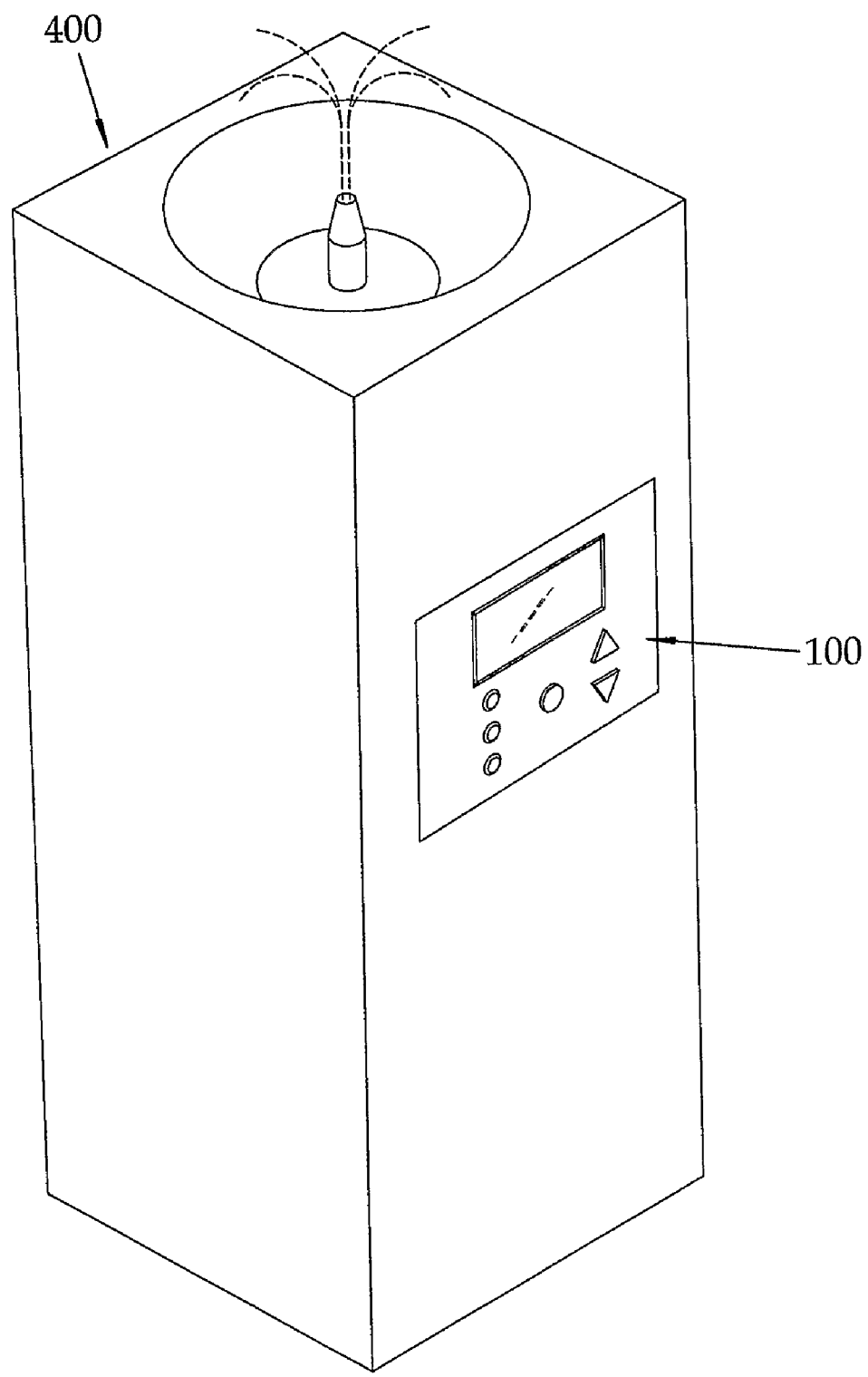
FIG. 9 is a view showing that the apparatus for measuring optimum water-quality and informing quality of the water is used for water feeder for drinking.

Also, the apparatus for measuring optimum water-quality and informing quality of water 100 may be installed on a water feeder for drinking 400 as shown in FIG. 9 and can display the quality of the water fed by the water feeder 400. Accordingly, a user can recognize the quality of the water fed by the water feeder 400 and decide whether to drink.

Further, the apparatus for measuring optimum water-quality and informing quality of water 100 may be installed in a refrigerator and inform the quality of the water fed by the refrigerator for drinking.

According to the present invention, the apparatus for measuring optimum water-quality and informing quality of water 100 can have a self power-generation which generates power by the flow of the water supplied thereto and is operated by the self generated power. In the self-power generation, the flow of the water supplied thereto drives a rotator and the physical energy of the driven rotator (kinetic energy) is converted to electrical energy.

According to the present invention, the apparatus for measuring optimum water-quality and informing quality of water 100 can inform the water quality by sound as well as the display. For example, it alarms sound if the present amount of the impurities of the water is larger than the optimum value. In another case, it sounds music or voice when the present amount of the impurities of the water arrives at the value smaller than the optimum value.

Figure 10:
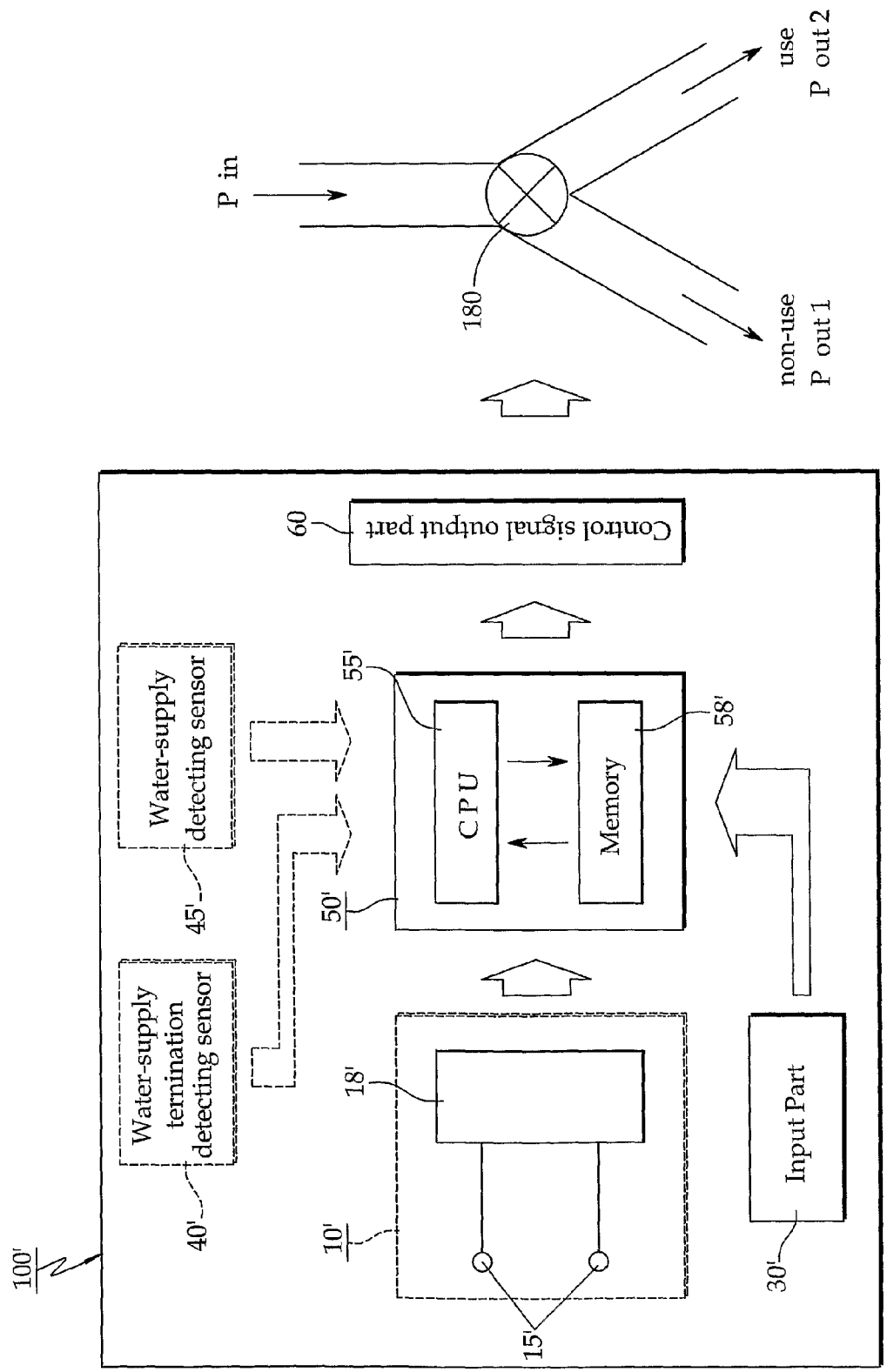
FIG. 10 is a view showing configuration of an apparatus for measuring optimum water-quality and control in accordance with an embodiment of the present invention.

The present invention provides an apparatus for measuring optimum water-quality and control 100' which keeps to renew an optimum water-quality value, compares a present amount of impurities of water with the optimum value and controls an actuator according to the comparison result. FIG. 10 shows an example of such an apparatus.

In this case, the apparatus for measuring optimum water-quality and control 100' includes an impurities-detecting part 10' which has a detecting terminal 15' and a circuit part 18' electrically processing the signal from the detecting terminal 15'.

Also, a control part 50' including a CPU 55' and a memory 58' is provided so that it keeps to renew the optimum value for the water-quality and compares the present amount of the impurities of the water with the optimum value by the same way as the apparatus for measuring optimum water-quality and informing quality of water 100 does as described before.

A water-supply termination detecting sensor 40' may be provided for deciding that it is the renewal time if the water-supply is terminated. Also, a water-supply detecting sensor 45 may be provided for operating the apparatus 100' only when the water is supplied.

The apparatus for measuring optimum water-quality and control 100' includes a control signal output part 60 coupled with the control part 50' and the control part 50' compares the present amount of the impurities of the water with the optimum value and controls the actuator through the control signal output part 60 according to the result.

For example, as shown in FIG. 10, in a case that a pipe $P_{in}$ to which water is supplied is diverged into two pipes $P_{out1}$ and $P_{out2}$, a valve 180 is installed at place where the pipe $P_{in}$ is diverged as the actuator and the vale 180 is controlled by the apparatus 100'.

If the present amount of the impurities of the water supplied to the pipe $P_{in}$ is smaller than the optimum value, the control part 50' controls the valve 180 to open the pipe $P_{out2}$ for use and, otherwise, the control part 50' controls the valve 180 to open the pipe $P_{out1}$ for non-use. The water flowing along the pipe $P_{out1}$ for non-use will be exhausted or supplied to a water-purifying filter or to a water purifier.

This way to diverge the water into use if the water-quality is good and into the water purifier, otherwise is very efficient when compared with the conventional way to purifying all the water. According to the present invention, the apparatus for measuring optimum water-quality and informing quality of water 100 includes a network interface part (not shown) and can be connected with a management computer (not shown) via wire or wireless communication means. The connection is made by, for example, wire or wireless Internet or non-contact communication such as bluetooth.

In this case, the control part 50 may store the present amount of the impurities of water or the optimum value by every time. Further, the control part 50 may send the present amount of the impurities of water or the optimum value by every time to the management computer.

In this case, the management computer can receive data related to water quality from the apparatuses for measuring optimum water-quality and informing quality of water 100 installed at many places and manage them.

Figure 11:
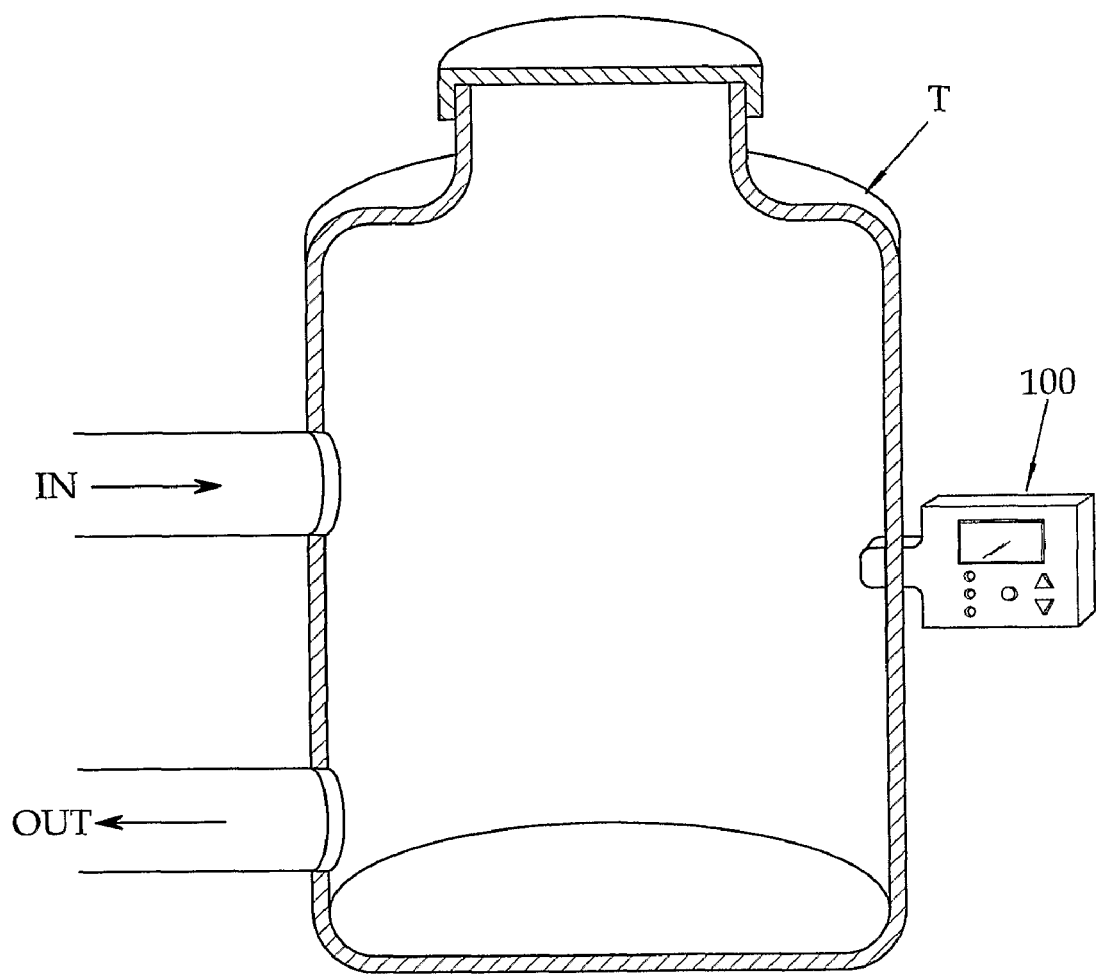
FIGS. 11 and 12 are views showing installation example of the apparatus for measuring optimum water-quality and informing quality of the water.
Figure 12:
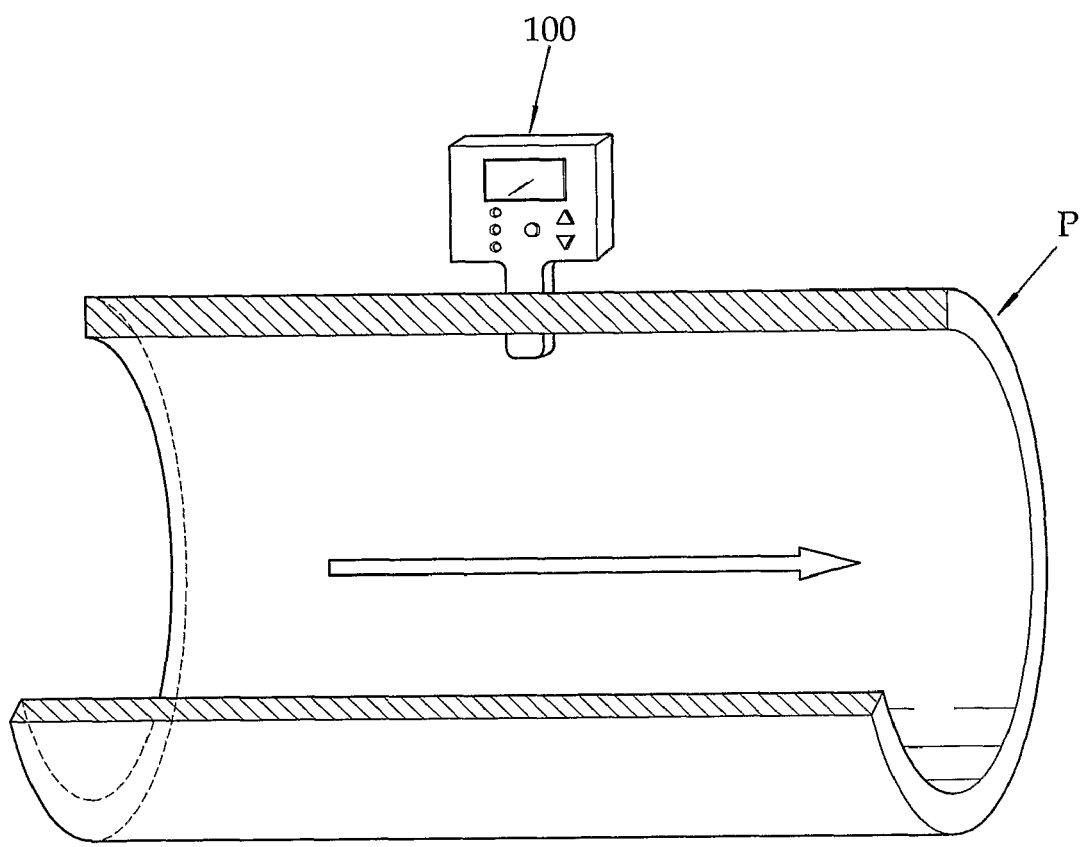

FIGS. 11 and 12 are views showing installation example of the apparatus for measuring optimum water-quality and informing quality of the water 100.

As shown in FIG. 11, the apparatus for measuring optimum water-quality and informing quality of the water 100 can be installed in a tank T by the inserting way.

Also, as shown in FIG. 12, the apparatus for measuring optimum water-quality and informing quality of the water 100 can be installed in a pipe P by the inserting way.

INDUSTRIAL APPLICABILITY

As described above, the present invention provides the apparatus and method which checks whether the water discharged from the particular water service pipe contains the lowest impurities among the discharged water until present time and informs the present quality of the discharged water.

The present invention is mainly applicable for tap water, however, not limited thereto.

The present invention is not the simple apparatus which compares the present impurities of water with the set value and displays that the water quality is good if the present impurities is below the set value. Instead, the present invention searches the lowest impurities of the water which the water service pipe can accomplish from the past use to the present use and informs that the water is optimum if the impurities of the water are below the lowest impurities. Accordingly, the present invention has an evolution type characteristic that it satisfies the more strict water quality standard as the use of the water service pipe is longer. Further, the present invention makes it possible to deal with a water pollution accident since, in that case, the present amount of the impurities of the water is highly above the optimum value, which can be noticed and it takes time for the apparatus according to the present invention to display the optimum status.

Therefore, it is understood that the purpose of the present invention is accomplished. The present invention is described with reference to the specific embodiments, but the invention is not limited there to. Only the following claims will determine the scope of the invention.

The invention claimed is:

1. An apparatus for measuring optimum water-quality and informing quality of water comprising:
    (a) an impurities-detecting part for detecting an amount of impurities of water;
    (b) a control part coupled with the impurities-detecting part, wherein the control part stores an initial optimum value, the optimum value indicating the optimum amount of the impurities of the water, the control part including,
    (b1) measurement means for measuring the amount of the impurities of the water which receives a signal for the amount of the impurities of the water from the impurities-detecting part and measures it,
    (b2) renewal time decision means for deciding whether it is a renewal time of the optimum value,
    (b3) comparison means for comparing the amount of the impurities of the water measured by the measurement means with the optimum value, and
    (b4) optimum-value renewal means for renewing the optimum value by the amount of the impurities of the water if the comparison result made by the comparison means is that the amount of the impurities of the water is smaller than the optimum value, if it is decided as the renewal time by the renewal time decision means;
    (c) informing part for informing the result of the comparison by the comparison means.

2. The apparatus for measuring optimum water-quality and informing quality of water as recited in claim 1 wherein the control part stores a renewal period and the renewal time decision means includes renewal time decision means by renewal period which decides the renewal time by every renewal period.

3. The apparatus for measuring optimum water-quality and informing quality of water as recited in claim 2 further comprising an input part for setting the renewal period coupled with the control part.

4. The apparatus for measuring optimum water-quality and informing quality of water as recited in claim 1 or 2 wherein it further includes an input part for requesting the renewal coupled with the control part and the renewal time decision means includes renewal time decision means by input of the renewal request which decides as the renewal time if the renewal request is inputted by the input part for requesting the renewal.

5. The apparatus for measuring optimum water-quality and informing quality of water as recited in claim 1 wherein it further includes a water-supply termination detecting sensor for detecting whether the water-supply is terminated coupled with the control part and the renewal time decision means includes renewal time decision means by the termination of the water-supply which decides as the renewal time if it is decided that the water-supply is terminated according to the water-supply termination detecting sensor.

6. The apparatus for measuring optimum water-quality and informing quality of water as recited in claim 5 wherein the water-supply termination detecting sensor is a current meter and the renewal time decision means by the termination of the water-supply decides as the renewal time if fluid velocity detected by the current meter is below a particular value.

7. The apparatus for measuring optimum water-quality and informing quality of water as recited in claim 6 wherein it further comprises a pipe part having a stay part at which the flowing water stays is formed and a detecting terminal of the impurities-detecting part is placed at the stay part.

8. The apparatus for measuring optimum water-quality and informing quality of water as recited in claim 5 wherein the impurities-detecting part detects an electric conductivity of the water and this impurities-detecting part is used as the water-supply termination sensor, and the renewal time decision means by the termination of the water-supply decides as the renewal time if the conductivity of the water detected by the impurities-detecting part is below a particular value.

9. The apparatus for measuring optimum water-quality and informing quality of water as recited in claim 5 wherein the impurities-detecting part detects a turbidity of the water and this impurities-detecting part is used as the water-supply termination sensor, and the renewal time decision means by the termination of the water-supply decides as the renewal time if the turbidity of the water detected by the impurities-detecting part is below a particular value.

10. The apparatus for measuring optimum water-quality and informing quality of water as recited in claim 5 wherein the water-supply termination detecting sensor includes an electrode and a circuit part for sensing conductivity of the water flowing around the electrode and the renewal time decision means by the termination of the water-supply decides as the renewal time if the conductivity of the water is below a particular value.

11. The apparatus for measuring optimum water-quality and informing quality of water as recited in claim 1 wherein the impurities-detecting part detects an electric conductivity of the water.

12. The apparatus for measuring optimum water-quality and informing quality of water as recited in claim 1 wherein the impurities-detecting part detects a turbidity of the water.

13. The apparatus for measuring optimum water-quality and informing quality of water as recited in claim 1 wherein the impurities-detecting part detects residual chlorine of the water.

14. The apparatus for measuring optimum water-quality and informing quality of water as recited in claim 1 wherein the impurities-detecting part detects an ion concentration for particular ion of the water.

15. The apparatus for measuring optimum water-quality and informing quality of water as recited in claim 1 wherein the impurities-detecting part detects a hydrogen ion concentration (PH) of the water.

16. The apparatus for measuring optimum water-quality and informing quality of water as recited in claim 1 wherein, if attribute of the impurities detected by the impurities-detecting part has allowable range according to water quality standard, the optimum value is determined by an absolute value of deviation of the allowable value from an inherent optimum value and the amount of the impurities of the water is determined by an absolute value of deviation of the amount of the impurities of the water from the inherent optimum value.

17. The apparatus for measuring optimum water-quality and informing quality of water as recited in claim 16 wherein the impurities-detecting part detects a hydrogen ion concentration (PH) of the water.

18. The apparatus for measuring optimum water-quality and informing quality of water as recited in claim 1 wherein the informing part informs that the water quality is good if the amount of the impurities of the water is smaller than the optimum value.

19. The apparatus for measuring optimum water-quality and informing quality of water as recited in claim 1 or 18 wherein the informing part informs whether the water is suitable according to water quality standard.

20. The apparatus for measuring optimum water-quality and informing quality of water as recited in claim 1 wherein the informing part informs that the water-quality is good if deviation of the amount of the impurities of the water from the optimum value is within some range.

21. The apparatus for measuring optimum water-quality and informing quality of water as recited in claim 1 further comprising a reset part for initializing the optimum value.

22. The apparatus for measuring optimum water-quality and informing quality of water as recited in claim 1 wherein it is installed in a water purifier or a water feeder for drinking.

23. The apparatus for measuring optimum water-quality and informing quality of water as recited in claim 1 further comprising a water-supply detecting sensor for detecting whether the water is supplied.

24. The apparatus for measuring optimum water-quality and informing quality of water as recited in claim 23 wherein the water-supply detecting sensor is a water-flow detecting sensor.

25. The apparatus for measuring optimum water-quality and informing quality of water as recited in claim 24 wherein the water-flow detecting sensor includes a buoyancy mechanism and a relay connected therewith.

26. The apparatus for measuring optimum water-quality and informing quality of water as recited in claim 1 wherein it further includes a self power-generation which generates power by the flow of the water supplied thereto and is operated by the self generated power.

27. An apparatus for measuring optimum water-quality and control comprising:
(a) an impurities-detecting part for detecting an amount of impurities of water;
(b) a control part coupled with the impurities-detecting part, wherein the control part stores an initial optimum value, the optimum value indicating the optimum amount of the impurities of the water, the control part including,
(b1) measurement means for measuring the amount of the impurities of the water which receives a signal for the amount of the impurities of the water from the impurities-detecting part and measures it,
(b2) renewal time decision means for deciding whether it is a renewal time of the optimum value,
(b3) comparison means for comparing the amount of the impurities of the water measured by the measurement means with the optimum value, and
(b4) optimum-value renewal means for renewing the optimum value by the amount of the impurities if the amount of the impurities of the water measured by the measurement means is smaller than the optimum value, if it is decided as the renewal time by the renewal time decision means;

(c) control-signal output part for outputting a control signal for controlling an actuator according to the result of the comparison by the comparison means.

28. A method for measuring optimum water-quality and informing quality of water comprising:
   (a) initial optimum value storage step where a control part stores an initial optimum value, the optimum value indicating the optimum amount of the impurities of the water;
   (b) impurities measurement step where the control part measures an amount of impurities of water by a signal from an impurities-detecting sensor for detecting an amount of impurities of the water;
   (c) renewal time decision step where the control part decides whether it is a renewal time of the optimum value;
   (d) comparison step where the control part compares the amount of the impurities of the water with the optimum value;
   (e) optimum-value renewal step where the control part renews the optimum value by the amount of the impurities if the amount of the impurities of the water measured by the measurement means is smaller than the optimum value, if it is decided as the renewal time by the renewal time decision step;
   (f) optimum water-quality inform step where the control part informs the result of the comparison by the comparison step through an informing part.

29. The method for measuring optimum water-quality and informing quality of water as recited in claim 28 wherein the renewal time decision step includes renewal time decision step by termination of water-supply where the control part decides as the renewal time if it is decided that the water-supply is terminated according to a water-supply termination detecting sensor for detecting whether the water-supply is terminated.

30. The method for measuring optimum water-quality and informing quality of water as recited in claim 28 wherein the renewal time decision step includes renewal time decision step by renewal period where the control part stores a renewal time and it decides the renewal time by every renewal period.

31. The method for measuring optimum water-quality and informing quality of water as recited in claim 28 wherein the renewal time decision step includes renewal time decision step by input of renewal request where the control part decides as the renewal time if the renewal request is inputted.

32. Computer readable storage medium recording the steps recited in one of claims 28 to 31.

33. A management computer connected with an apparatus for measuring optimum water-quality and informing quality of water via communication network, the management computer managing data received from the apparatus, the apparatus comprising:
   (a) an impurities-detecting part for detecting an amount of impurities of water;
   (b) a control part coupled with the impurities-detecting part, wherein the control part stores an initial optimum value, the optimum value indicating the optimum amount of the impurities of the water, the control part including,
   (b1) measurement means for measuring the amount of the impurities of the water which receives a signal for the amount of the impurities of the water from the impurities-detecting part and measures it,
   (b2) renewal time decision means for deciding whether it is a renewal time of the optimum value,
   (b3) comparison means for comparing the amount of the impurities of the water measured by the measurement means with the optimum value, and
   (b4) optimum-value renewal means for renewing the optimum value by the amount of the impurities if the amount of the impurities of the water measured by the measurement means is smaller than the optimum value, if it is decided as the renewal time by the renewal time decision means;
   (b5) impurities storage means by every time for storing the amount of the impurities of water by every time;
   (b6) impurities-data sending means for sending the amount of the impurities of the water stored by the impurities storage means to the management computer.

34. The management computer recited in claim 33 wherein the control part of the apparatus further including optimum value storage means for storing the optimum value by every time and optimum-value data sending means for sending the optimum value stored by the impurities storage means to the management computer.

* * * * *